United States Patent [19]

Dussault

[11] Patent Number: 5,261,415
[45] Date of Patent: Nov. 16, 1993

[54] $CO_2$ MAINSTREAM CAPNOGRAPHY SENSOR

[75] Inventor: Richard A. Dussault, North Attleborough, Mass.

[73] Assignee: Ciba Corning Diagnostics Corp., Medfield, Mass.

[21] Appl. No.: 729,509

[22] Filed: Jul. 12, 1991

[51] Int. Cl.$^5$ .............................................. A61B 5/08
[52] U.S. Cl. ................................... 128/719; 128/633; 128/664; 422/84; 73/23.3
[58] Field of Search .............. 128/719, 633, 664, 716; 606/3; 73/23.21, 23.23, 23.3; 356/436–439; 422/84; 374/133

[56] References Cited

U.S. PATENT DOCUMENTS

| | | | |
|---|---|---|---|
| 3,922,656 | 11/1975 | Horvath | 340/237 S |
| 4,050,823 | 9/1977 | Frankenberger | 356/186 |
| 4,180,734 | 12/1979 | Gedeon | 128/719 X |
| 4,370,553 | 1/1983 | Waycaster | 250/343 |
| 4,423,739 | 1/1984 | Passaro | 128/719 |
| 4,549,553 | 10/1985 | Hochberg | 128/719 |
| 4,590,374 | 5/1986 | Brewster | 250/338 |
| 4,648,396 | 3/1987 | Raemer | 128/719 X |
| 4,677,987 | 7/1987 | Choksi | 128/719 |
| 4,760,250 | 7/1988 | Loeppert | 250/227 |
| 4,821,736 | 4/1989 | Watson | 128/719 |
| 4,859,859 | 8/1989 | Knodle | 250/504 R |
| 4,914,720 | 4/1990 | Knodle et al. | 356/437 X |
| 4,928,687 | 5/1990 | Lampotang | 128/207.14 |
| 4,955,946 | 9/1990 | Mount et al. | 128/719 |
| 4,998,018 | 3/1991 | Kurahashi et al. | 128/719 X |

*Primary Examiner*—Lee S. Cohen
*Assistant Examiner*—Brian L. Casler
*Attorney, Agent, or Firm*—Arthur S. Morgenstern; Nicholas I. Slepchuk, Jr.; Charles L. Gagnebin, III

[57] ABSTRACT

A capnography system has a 4.2 micron LED emitter of narrow-band radiation having a center wavelength very close to the 4.26 micron absorption band of $CO_2$ breathing gas in a breathing tube. The radiation passes through windows in an insert in the breathing passage between the LED source and an infrared detector in an opposite side of the insert. A mirror is optionally placed in the opposite wall to reflect the radiation back to the detector which is then placed on the same side as the emitter. The LED emitter is pulsed at a low frequency repetition rate with a regulated voltage from a power supply. The detector output is applied to processing electronics which includes amplification and dual integrators that integrate the detector output on two signal paths, one the integration of each pulse and the other the integration of detector background with the two differences to provide self calibration against drift and noise. A heater heats the emitter, infrared detector, local electronics and the windows thereby stabilizing these temperature sensitive components to minimize the measured $CO_2$ value error to a few mm of mercury and to prevent condensation on the insert particularly in the windows. A second emitter is optionally used as a reference and/or to detect additional gas concentrations.

52 Claims, 7 Drawing Sheets

FIG. 7

CO2 MAINSTREAM CAPNOGRAPHY SENSOR

FIELD AND BACKGROUND OF THE INVENTION

The present invention relates to capnography in which the concentration of $CO_2$ in breathing gases is monitored during surgery or for other medical procedures or evaluation. The concentration detection point is advantageously as close to the mouth as possible necessitating a small lightweight unit capable of being placed close to the mouth. The traditional in-line manner of making this measurement is by emitting in the infrared from a heated body, filtering the broadband radiation to the $CO_2$ absorption band, applying it through a section of the passage from the breathing gases and detecting the change in level of the radiation caused by selective absorption by $CO_2$. The heated bodies generate much energy in bands where it cannot be used and are subject to problems of aging. The filters are another element in the system that are sources of expense, errors from temperature variation and contamination if not properly sealed. The detectors for the IR range are very temperature dependent and noisy. Mechanical chopping techniques have been used in the past to avoid DC drift errors but are expensive and unreliable.

LED emitters are available in the near IR range, but emitters of appropriate frequency and narrowness in the band of interest have not been available, so that the emitter or source of choice continues to be the heated black or grey body.

BRIEF SUMMARY OF THE INVENTION

According to the teaching of the present invention, a capnography system is disclosed in which a passage for breathing gases to and from a patient has an insert with windows in its opposite walls. A newly available LED emitter which not only radiates at 4.2 microns in the IR but has a narrow band output that coincides with the $CO_2$ absorption band is placed to pass radiation into the passage within the insert through a window and a detector receives that radiation through an opposite window. To increase the radiation path length through the gases, a reflector is optionally placed behind the opposite window and the radiation returned to the detector through the first or an adjacent window.

A heater and regulator (or optionally a cooler) maintains the temperature of the detector within $\pm 0.01°$ C. to a preset value, limiting the detector output to be subject to a maximum error of 2–3 mmHg of $CO_2$ for an eight-hour period. The emitter is also preferably temperature controlled to minimize drift induced errors.

A precision voltage source with a high current drive capability powers the LED emitter at a controlled pulse excitation at typically 500 Hz. Processing electronics is responsive to the detector output and includes a surface mounted amplifier or preamplifier on the same substrate as the infrared detector. A second amplifier is remotely located, and its output is applied to a pair of integrators. The first integrator integrates the amplified pulse output of the detector and the second integrates the amplified background signal. The two integrations are differenced to minimize drift and noise errors and then sampled and held for at least the duration between pulses. This signal is then low pass filtered to further eliminate noise. The resulting output is an electrical representation of a capnogram or graphical printout of the $CO_2$ concentration of each breath.

Further emitters are optionally provided to emit at a reference frequency or the absorption frequency of another gas. In the case of a reference beam, the detector outputs are ratioed to provide further noise immunity and compensate for gain variations in the transfer function of the optical system. In the case of a further emitter at an absorption band for another gas, similar processing electronics are typically used. In either case, the outputs may be applied to a recording or data processing system, alarm, or other instrumentation as desired.

DESCRIPTION OF THE DRAWING

These and other features of the present invention are more fully described below in conjunction with the accompanying drawing of which.

DETAILED DESCRIPTION

The present invention describes a capnography system in which the $CO_2$ concentration in breathing gases is detected using infrared absorption from a narrow band LED emitter that has a spectral output suitably tuned to the 4.26 microns $CO_2$ absorption band so that no filters are required and minimum energy beyond that required for absorption is generated. The radiation passing through breathing gases is detected and a detector signal processed with an integration characteristic that provides noise and drift immunity and results in an output capnogram representation of $CO_2$ concentrations. For increased absorption efficiency a reflector is used in the passage for breathing gases to permit multiple traversals by the radiation and to permit locating detector and emitter close to each other. The proximity of detector and emitter facilitates regulating their temperature which provides stability resulting in higher precision over time.

In accordance with the invention as illustrated in FIGS. 1, 1A, 2A and 2B there is provided in a breathing passage 12 having a tube 14 which conducts breathing gases to and from a patient's airway and a tube 16 which transports those gases to and from exhaust ports 18 and mixture inputs 20. An insert 22 therebetween has a center portion through which the breathing gases pass in a flow column 24. A housing 26, in a substantially horseshoe shape, surrounds the insert 22. The insert 22 has opposite side windows 28 and 30 which are aligned with apertures 32 and 34 within an inner collar 62 of the housing 26 and through which radiation passes from an emitter 36, typically in a TO 39 canister, to a detector 38 in a similar package. Optics assemblies 40 and 42 containing optics more fully illustrated in FIG. 3, focus and direct the radiation through the windows 32 and 34 and in turn through windows 28 and 30 of the insert 22.

Figure 1:
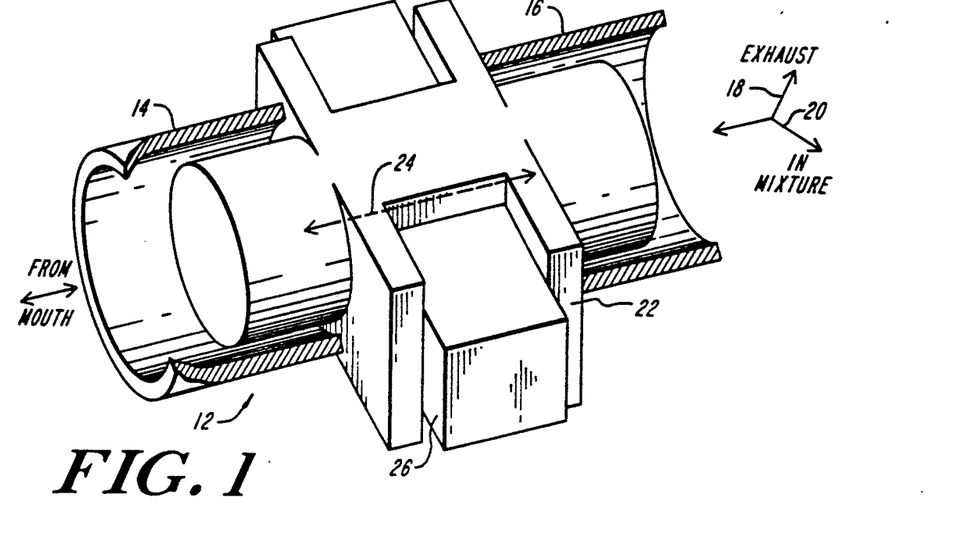
FIG. 1 is an illustration of an assembly of insert and housing for use in the invention.
Figure 1A:
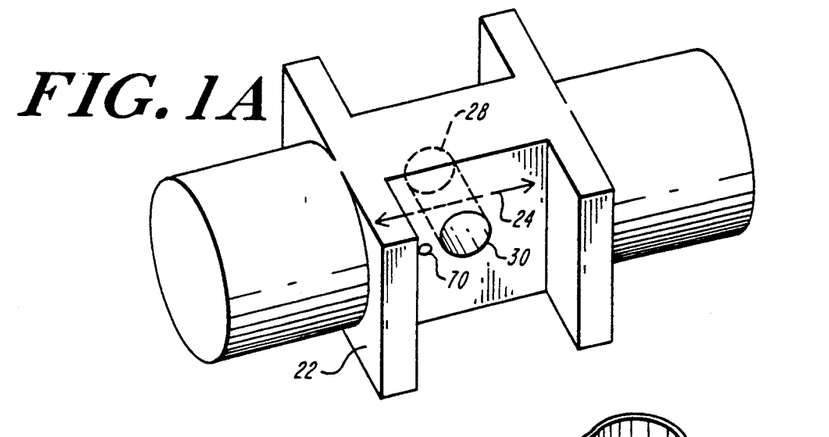
FIG. 1A is an illustration of the breathing passage insert.
Figure 2A:
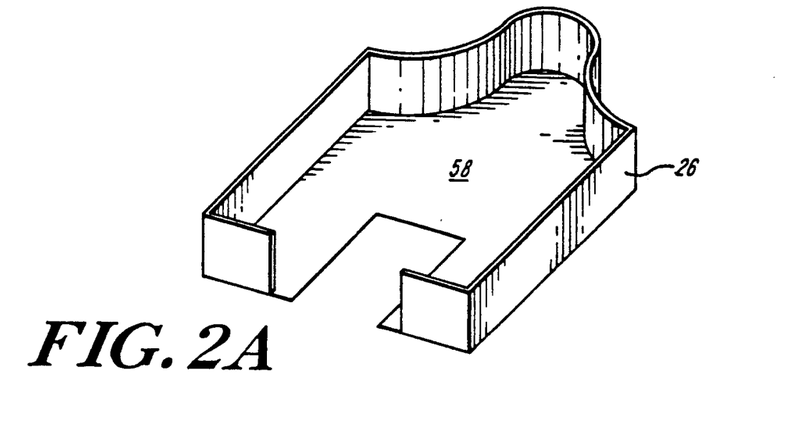
FIG. 2A and FIG. 2B are illustrations of the housing for IR emitters, detectors, and a heater used in conjunction with the insert.
Figure 2B:
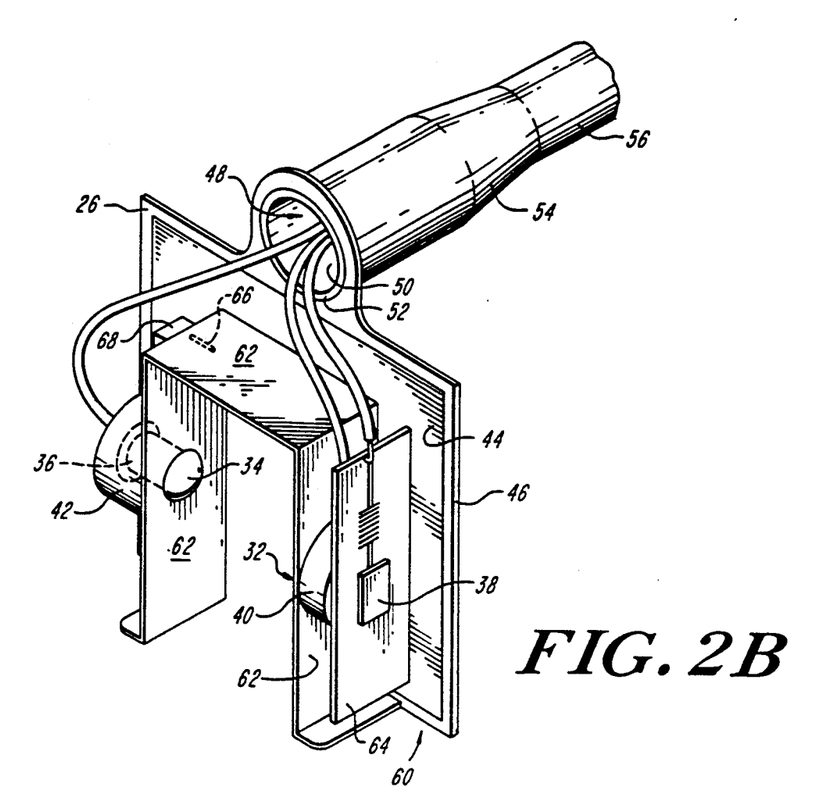

The emitter 36 is an LED emitter which emits with a spectral profile centered at 4.2 microns and is typically and preferably an emitter provided by Laser Monitoring Systems Limited of Huntington Road, Cambridge, England, and comprises an InAsSbP/InAs solid state emitter. The detector 38 may be any of the conventional detectors utilized for receiving IR signals in the spectral range of interest.

Because of the detector's substantial thermal sensitivity, its temperature is controlled by a U-shaped heater blanket 44 placed adjacent a wall 46 of the housing 26. Electrical signals to the emitter 36, detector 38, and heater blanket 44 pass via cabling 48 through an aperture 50 in a tab 52 on the wall 46 and are protected by a grommet 54 before entering a cable 56 to electronics located remotely and shown in FIG. 5.

The housing 26 as illustrated in FIGS. 2A and 2B is composed of a cover portion 58 and an electronics portion 60 of which the wall 46 is a part. In order to promote thermal conduction from the blanket 44 to collar 62 to heat the emitter 36 and detector 38 for thermal control and to heat the windows 28 and 30 in the range of 38°-41° C. to prevent condensation of breathing gases, the inner material for the housing 26 and collar 62 should be of good thermal conductivity. This may be achieved by the use of a good thermally conductive plastic such as a metal filled VALOX (a trademark of EI DuPont De Nemours & Co.) or by an anodized metal. The outer surface is typically electrically non-conducting with a low thermal conductivity.

The detector 38 is mounted to a circuit board 64 and has associated with it, typically on the same substrate as the detection element, a surface mounted amplifier to provide buffering and preamplification. Other circuit elements as appropriate to local biasing, etc. may be mounted on the circuit board 64 as well.

Figure 3:
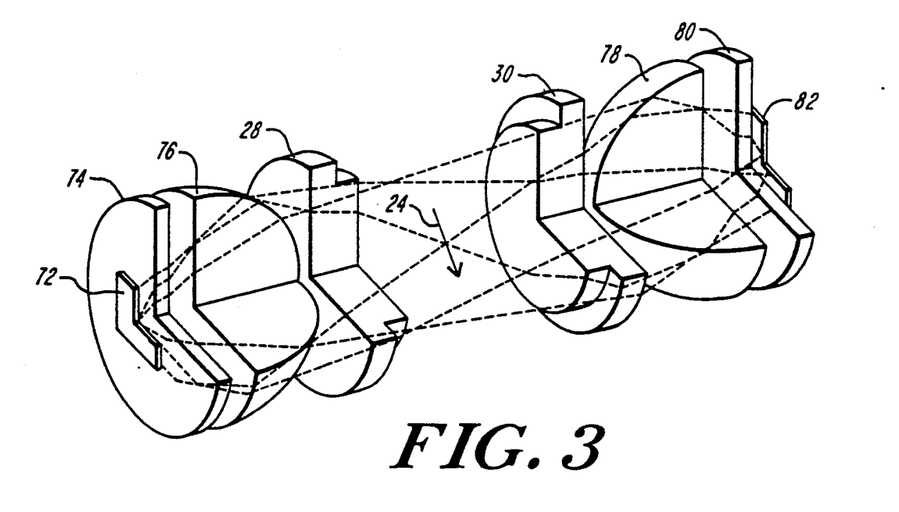
FIG. 3 is an illustration of optics in the radiation path between emitter and detector in the housing of FIGS. 2A and 2B.

FIG. 3 illustrates the optics of the system of the present invention. In particular the emitter is provided in a TO package having an emitting semiconductor die element 72 which is preferably placed close to a sapphire window 74 of the package. Within the housing 42 a sapphire lens 76 provides focussing of the radiation to pass through the flow zone 24 with optimal intensity after passing through the sapphire window 28 in the insert 22. The radiation exits the insert 22 through the sapphire window 30 and is reconverged by a sapphire lens 78 in the housing 40 for application through a sapphire window 80 in the TO packaging of the detector 38 which in turn has the photosensitive die 82 located close to the window 80 in its package.

Figure 4A:
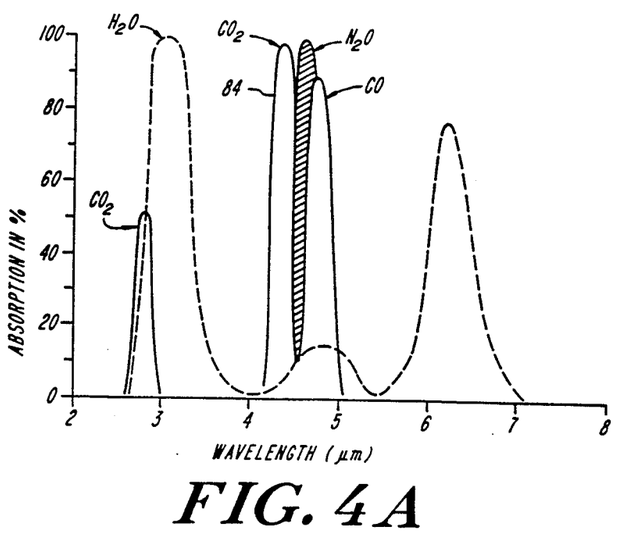
FIGS. 4A and 4B are absorption and emission profiles useful in explaining the invention.
Figure 4B:
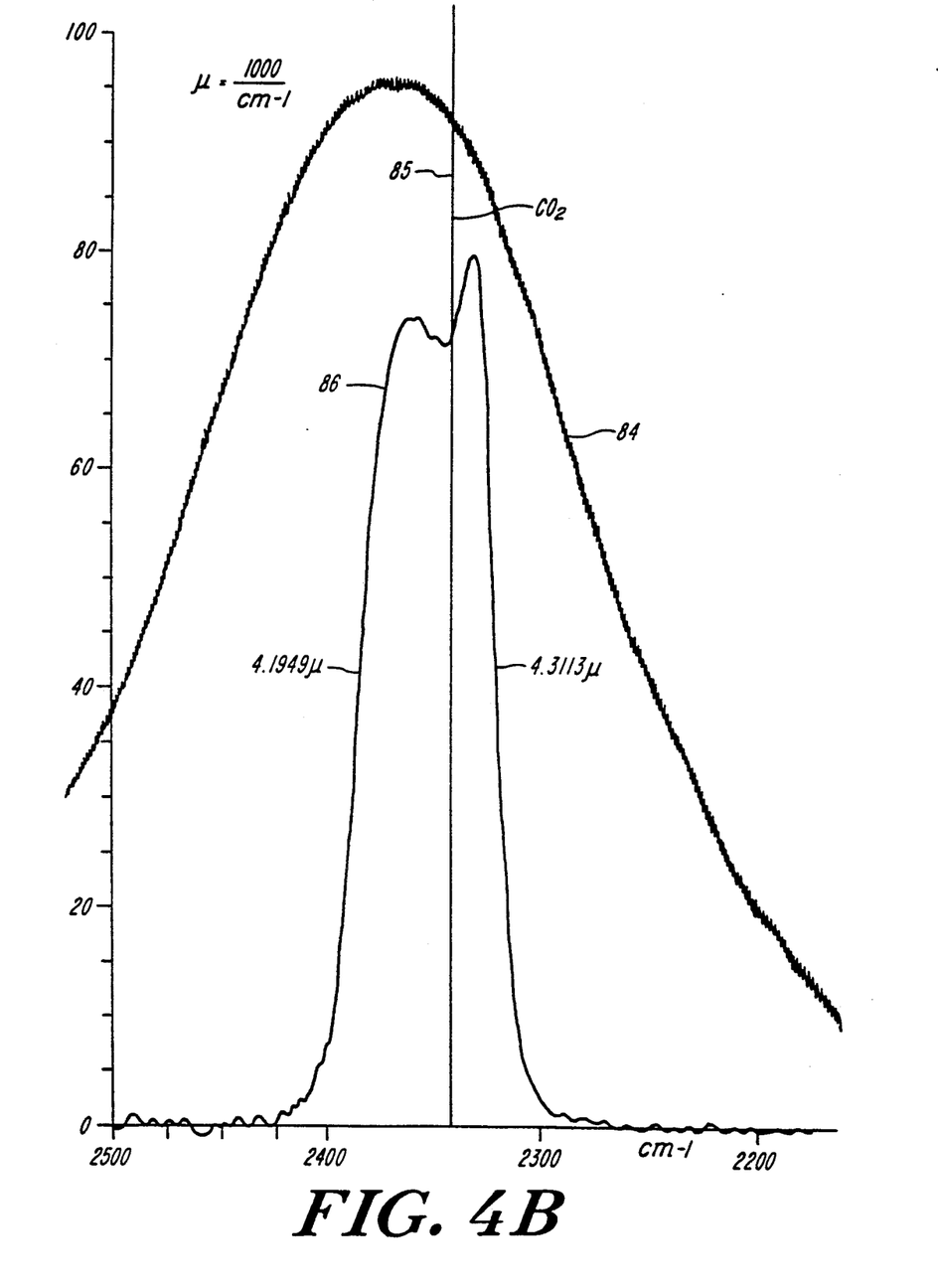

As illustrated in FIGS. 4A and 4B the absorption bands for the various gases, $H_2O$, $CO_2$, CO, and $N_2O$ in breathing gases are illustrated. $CO_2$ has a spectral peak response 84 in the region of approximately 4.1 to 4.4 microns. The LED emitter of preference, and only recently available, has a spectral output characteristic 86 which encompasses the $CO_2$ absorption band which is distributed about a center frequency 85. The emitter LED's spectral output is significantly narrow and so does not react with other gases that may be present in the airway gases.

Prior systems for capnography have utilized heated elements such as metal wires or plates as the only radiating elements or aid at this wavelength and these in turn have provided broad spectrum radiation which must in turn be filtered by the additional complexity of an expensive filter in order to achieve a narrow band 84 of filtered radiation and avoid radiation striking the detector in regions where no signal representative of $CO_2$ concentration is provided and thus creating suboptimal conditions for selectivity, sensitivity, drift and background noise. The emitter of the present invention permits accessing the infrared peak 84 specifically in a region where $CO_2$ and only $CO_2$ is absorptive and wastes little additional energy outside the band. This provides a great increase in operational accuracy, reliability and economy of design.

Figure 5:
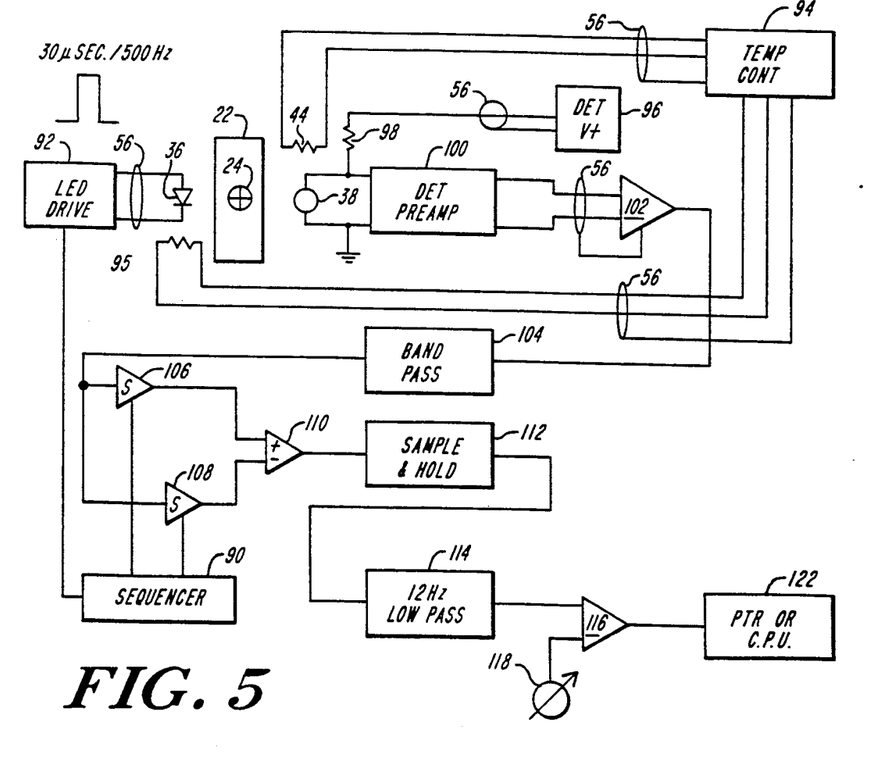
FIG. 5 is a block diagram of processing and power supply electronics of the capnography system of the invention.

With respect now to FIG. 5, there is illustrated the electronics associated with the capnography system of the present invention. A digital sequencer 90 provides pulse activation of an LED driver 92 to provide 500 Hz repetition rate power activation of the emitter 36 through the cabling 56. The pulse radiation passes through the insert 22 and the flow 24 and is received by the detector 38. A heater 44 is powered by a temperature controller 94 in response to temperature sensed by a sensor 95. Thermal regulation to 0.01° C. is provided by the controller 94 which in turn permits a maximum error of approximately 2 to 3 mmHg of $CO_2$ out of a typical 14 to 15 millimeters concentration over an eight hour period while at the same time preventing condensation from forming on the walls of the insert 22 and, preferably, thermal control of the emitter 36. For this purpose additional heater elements may be provided as desired along with associated sensors.

The solid state detector 38 is biased from a regulated power supply 96 through a biasing resistance 98. The voltage variation caused by radiation incident upon the detector 38 is applied through a preamplifier 100 which is typically a surface mounted preamplifier directly associated with the detector 38 as on the same chip or closely located thereto. The amplifier 100 provides a low gain, typically 3.8 out of a total 3800 gain, as well as impedance buffering. The preamplifier 100's output signal is applied through the cabling 56 to an amplifier 102 at the remotely located electronics. The amplifier 102 typically further boosts the signal with a gain of 1000 to achieve a desired 3800 amplification. The output of the amplifier 102 is applied through a band pass filter 104 which has a low frequency cutoff that accommodates the repetition rate of the LED emitter pulses and high frequency cutoff that limits noise while maintaining the square wave flat top characteristic of each detected radiation pulse.

The output of the band pass filter 104 is applied to first and second integrators 106 and 108. Integrator 106 provides integration of the pulse output from the detector 38 and is activated by the sequencer 90 to commence integration when the LED pulse starts and to stop integration when the LED pulse ceases. The integrator 108 provides integration of the background and it starts approximately 50 microseconds before the LED pulse activation and stops when the pulse is first turned on. The outputs of the integrators 106 and 108 are applied to respective noninverting and inverting inputs of a differential amplifier 110. The output of the amplifier 110 is then applied to a sample and hold circuit 112 which maintains the output level from the amplifier 110 in the interval between pulses. The net effect of the function of the two integrators 106 and 108 is to both filter out noise variations because of the high frequency attenuation characteristics of the integration and to continuously adjust against the background level provided by the integrator 108.

Figure 5A:
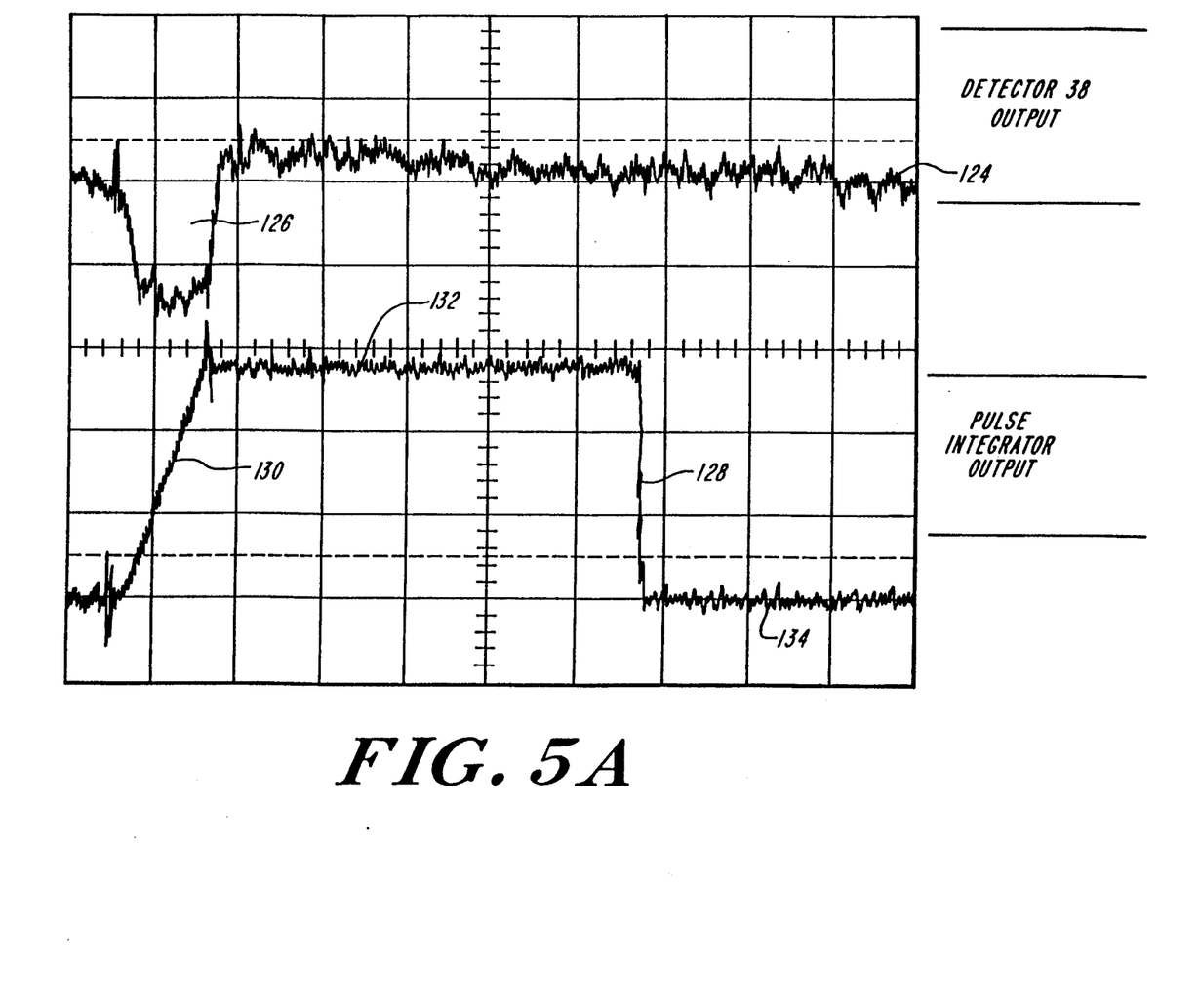
FIGS. 5A and 5B are waveform diagrams illustrating signals in the processing electronics of FIG. 5.

The operation of the integrators 106 and 108 along with amplifier 110 and sample and hold, circuits 112 are illustrated in FIG. 5A. As shown there, a trace 124 represents the output of the detector 38 and in particular a pulse 126 corresponds to the detection of the LED pulse of radiation. A waveform 128 has a ramp-up portion 130 corresponding to the output of the integrator 106 during the pulse 126. At the termination of the pulse 126 that level is held as a level 132 by the sample and hold circuit 112. The quiescent level at the output of the amplifier 110 as shown at portion 134 is adjusted to a nominal level by the integrator 108 correcting for background noise and drift through the differencing effect of the amplifier 110.

Figure 5B:
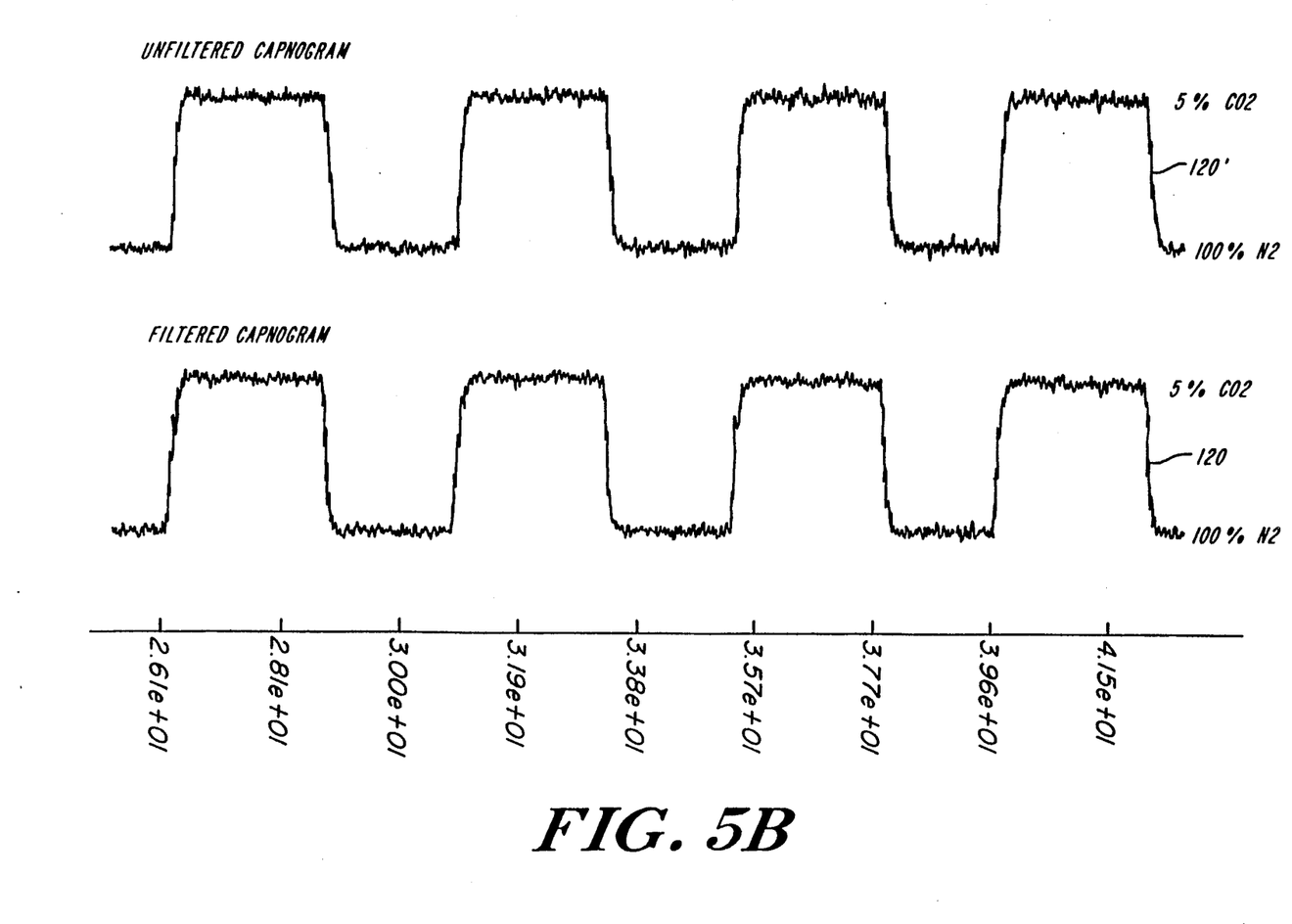

The output of the sample and hold circuit 112 is applied through a low pass filter 114 which has a cutoff around 12 Hz in order to remove all possible high frequency noise. The output of the filter 114 is applied through an amplifier 116 which has a level adjust 118 to permit adjustment of the output to a predetermined level (or zero) in a calibration setup with no $CO_2$ applied. The output of the amplifier 116, which is a signal representing a capnogram 120 (filtered, 120' unfiltered) of FIG. 5B, has a succession of square waves corresponding to each patient breathing cycle and a peak level representing the $CO_2$ concentration in the breathing. This signal is applied in turn to a utilization device 122 comprising a printer, a computer, computer driven data acquisition system or other unit as desired.

Figure 5C:
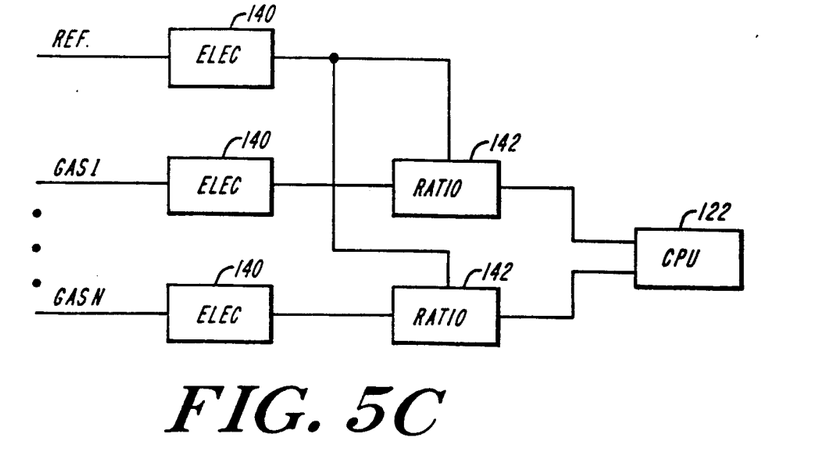
FIG. 5C is a block diagram for use with a multiple emitter and/or detector embodiment of the invention.

The present invention may utilize more than one emitter 36. Typically an emitter having an output spectrum corresponding to no absorption peak may be used as a reference emitter. Additional emitters may be used to detect other gases in the breathing passage. As illustrated in FIG. 5C the detector signals for those various gases would be applied through electronics 140 corresponding to the electronics of FIG. 5. In the case of a reference signal, the output of the electronics 140 corresponding to the reference would be ratioed or differenced in electronics 142 to adjust for any long term variations in system gain such as minor contamination of the lenses or deterioration of components before application to utilization electronics 122.

Figure 6:
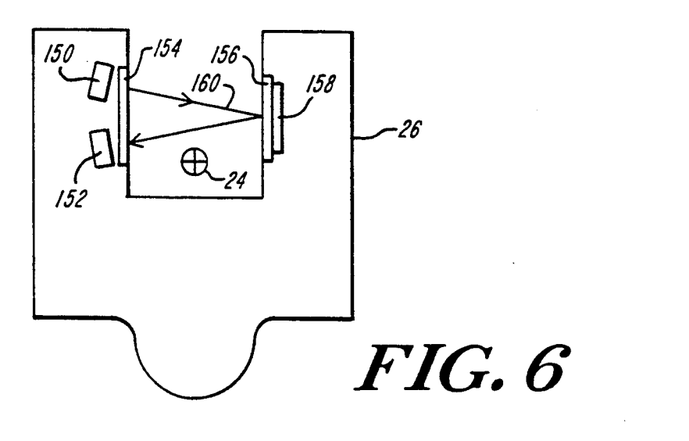
FIG. 6 illustrates an alternative housing configuration for using a reflector in the radiation path.

In an alternative emitter and detector configuration illustrated in FIG. 6, the housing 26 has an emitter 150 adjacent to a detector 152 on the sam side of the housing and directing radiation through a single, or possible plural windows, 154 to the other leg of the housing 26 through a window 156 for reflection by a mirror 158, typically a gold layer, or other reflector. In this manner, the radiation from the detector 152 experiences two traversals 160 of the flow 24 substantially increasing the opportunity for absorption and thereby increasing the signal to noise ratio of the overall capnography system.

Figure 7:
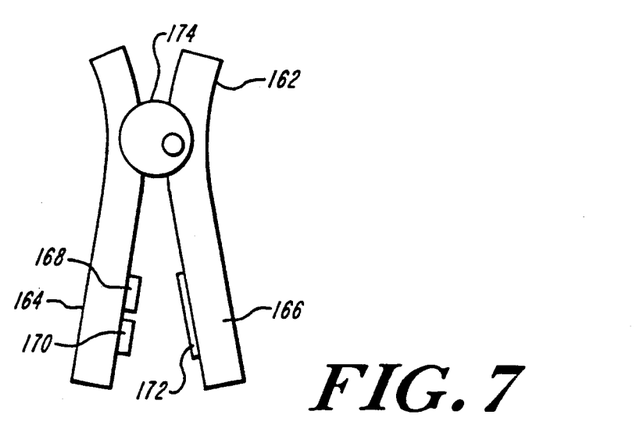
FIG. 7 illustrates a clip-on embodiment of the invention.

FIG. 7 illustrates a further embodiment for the housing design comprising a clip 162 having on fingers 164 and 166 respectively emitter detector pairs 168, 170 and reflector 172. The design of FIG. 7 is usable to clip directly onto transmissive tubing without the necessary set up time for providing a segmented breathing passage with the insert 22 therein, or may be utilized to clip onto such an insert in those cases where the insert is provided. The spring loading of the spring assembly 174 maintains the clip system in place.

The components utilized to heat the temperature sensitive components in the insert as described above may be replaced with thermoelectric or other cooling components to not only achieve the benefits of temperature regulation but to increase sensitivity and the signal to noise ratio at colder temperatures.

The above description is exemplary of one implementation only for the present invention. The claims are written to cover other implementations which fall within the scope of the invention.

I claim:
1. A capnography system comprising:
   a breathing passage for breathing gases between a patient and an exhaust;
   an optical path across said breathing passage permitting the transmission of radiation therethrough;
   an LED source of pulsed radiation, positioned adjacent said breathing passage, for emitting radiation of approximately 4.2 micron wavelength and of a bandwidth encompassing the absorption band of $CO_2$ in said optical path;
   a detector for pulsed radiation positioned adjacent said breathing passage for the receipt of radiation emitted by said LED source and to provide a pulsed waveform output in response to the received pulsed radiation from said LED source; and
   processing electronics electrically connected to said detector, said processing electronics responsive to the pulsed waveform output provided by said detector and generating an output capnogram representation of the concentration of $CO_2$ in said breathing passage.

2. The capnography system of claim 1 further including an insert cooperative with said breathing passage having at least one window disposed in the optical path of said breathing passage adjacent said LED source and at least one opposite optical element disposed in the optical path across said breathing passage from said at least one window selected from a group consisting of a window and a reflector.

3. The capnography system of claim 2 wherein said window is of sapphire.

4. The capnography system of claim 1 wherein said LED source is an InAsSbP/InAs emitter.

5. The capnography system of claim 4 wherein said LED is packaged in a TO housing with a sapphire window.

6. The capnography system of claim 1 further including:
   a heater cooperative with said detector for maintaining the temperature of the detector.

7. The capnography system of claim 6 wherein said heater has a regulator which maintains the detector temperature within a range to provide a maximum error of approximately 3 mmHg of $CO_2$ over eight hours in said capnogram representation.

8. The capnography system of claim 1 further including:
   a heater disposed adjacent said breathing passage for applying heat to said optical path to prevent condensation on said optical path from vapor in said breathing passage.

9. The capnography system of claim 1 further including:

a housing with said LED source and said detector removably mounted on said breathing passage for positioning said LED source to emit radiation across said optical path and for positioning said detector to receive the emitted radiation.

10. The capnography system of claim 9 further including a heat source disposed within said housing providing heat to said optical path when said housing is mounted to said breathing passage and for temperature control of at least one of said source and detector.

11. The capnography system of claim 10 further including a heater regulator connected to said heater for maintaining a temperature of the detector in said housing within approximately 0.01° C.

12. The capnography system of claim 1 wherein said processing electronics include:
a power supply connected to said LED source, said power supply being regulated in voltage to maintain a stable emission spectrum of radiation power level emitted by said LED source.

13. The capnography system of claim 1 wherein said processing electronics includes:
an amplifier connected to said detector to amplify the pulsed waveform output of said detector.

14. The capnography system of claim 13 wherein said amplifier is a surface mounted amplifier.

15. The capnography system of claim 1 wherein said processing electronics includes:
an integrator connected to integrate the pulsed waveform output of said detector above a repetitively adjusted baseline.

16. The capnography system of claim 15 wherein said processing electronics includes:
a sample and hold circuit connected to said integrator for the integrated pulse output of the detector.

17. The capnography system of claim 16 wherein said sample and hold circuit maintains each integrated pulse output between output pulses of the detector and further including:
a low-pass filter connected to said sample and hold circuit having a cut-off point below a pulse repetition rate of pulse emissions from the LED source.

18. The capnography system of claim 1 wherein:
said LED source includes a source of reference radiation sensed by said detector; and
said processing electronics provides the capnogram representation with compensation for the reference radiation as sensed by the detector.

19. The capnography system of claim 1 wherein:
said LED source includes a source of radiation for a further gas in said breathing passage which radiation is sensed by said detector; and
said processing electronics provides an output capnogram representation of the concentration of the further gas in the breathing passage.

20. A capnography system comprising:
a breathing passage for breathing gases between a patient and a breathing gas source and an exhaust;
an LED source of pulsed radiation positioned adjacent said breathing passage, the radiation having a narrow band emission spectrum coinciding with an absorption band of $CO_2$ gas within said breathing passage;
a detector positioned adjacent said breathing passage for detecting pulsed radiation from said LED source through said passage and providing a pulsed waveform output in response to the reception of pulsed radiation from said LED source;
a mirror mounted adjacent said breathing passage;
an optical access disposed transversely through said breathing passage enabling the transmission of radiation across said breathing passage between said LED source and said detector by reflection of the pulsed radiation by said mirror from an opposite side to provide multiple traversals through the breathing gas by said radiation;
processing electronics electrically connected to said detector, said processing electronics responsive to the pulsed waveform output provided by said detector and generating an output capnogram representation of the concentration of $CO_2$ in said breathing passage.

21. The capnography system of claim 20 wherein said optical access includes an insert disposed in said breathing passage adjacent said detector defining at least one window opposing said mirror across breathing passage.

22. The capnography system of claim 21 wherein each said window is of sapphire.

23. The capnography system of clam 20 wherein said LED source is an InAsSbP/InAs emitter.

24. The capnography system of claim 23 wherein said LED source is packaged in a TO housing with a sapphire window.

25. The capnography system of claim 20 further including:
a heater positioned adjacent said detector for maintaining the temperature of the detector.

26. The capnography system of claim 25 wherein said heater further includes a controller for maintaining the detector temperature within a range to provide a maximum error of approximately 3 mmHg of $CO_2$ over eight hours in said capnogram representation.

27. The capnography system of claim 20 further including:
a heater positioned adjacent said optical access for preventing condensation on said optical access mirror from vapor in said breathing passage.

28. The capnography system of claim 20 further including:
a housing for said LED source and said detector removably mounted with respect to said optical access to place said source and detector in radiation transmission and receiving relationship to gases in said breathing passage when mounted to said optical access.

29. The capnography system of claim 28 further including a heat source mounted within said housing providing heat to said optical access and to at least one of said source and detector.

30. The capnography system of claim 29 including a heater regulator cooperative with said housing for maintaining a temperature within said housing within approximately 0.01° C.

31. The capnography system of claim 20 wherein said processing electronics includes:
a power supply for said LED source cooperative with said processing electronics regulated in voltage to maintain an emission spectrum of said LED source.

32. The capnography system of claim 20 wherein said processing electronics includes:
an amplifier connected to said processing electronics and in close proximity to the detector for amplifying the detector pulsed waveform output.

33. The capnography system of claim 32 wherein said amplifier is a surface mounted amplifier.

34. The capnography system of claim 20 wherein said processing electronics includes:
an integrator connected to said processing electronics for integrating the pulsed waveform output of the detector above a repetitively adjusted baseline.

35. The capnography system of claim 34 wherein said processing electronics includes:
a sample and hold circuit connected to said processing electronics for holding the integrated pulsed waveform output of the detector.

36. The capnography system of claim 35 wherein said sample and hold circuit maintains each integrated pulse output between output pulses of the detector and further including:
a low pass filter having a cut-off point below a pulse repetition rate of pulsed emissions from the LED source.

37. The capnography system of claim 20 wherein:
said LED source includes a source of reference radiation sensed by said detector; and
said processing electronics provides the capnogram representation with compensation for the reference radiation as sensed by the detector.

38. The capnography system of claim 20 wherein:
said LED source further includes a source of radiation having a wavelength within the absorption band of a further gas in said breathing passage which radiation is sensed by said detector; and
said processing electronics provides an output capnogram representation of the concentration of the further gas in the breathing passage.

39. A capnography system comprising:
a breathing passage for breathing gases between a patient and a breathing gas source and an exhaust;
an LED source of pulsed radiation positioned adjacent said breathing passage, the radiation having a narrow band emission spectrum coinciding with an absorption band of $CO_2$ gas within said breathing passage;
a detector positioned adjacent said breathing passage for detecting pulsed radiation from said LED source through said passage and providing a pulsed waveform output in response to the reception of pulsed radiation from said LED source;
an optical access disposed transversely through said breathing passage providing for the transmission of radiation through said breathing passage between said LED source and said detector;
processing electronics electrically connected to said detector, said processing electronics responsive to the pulsed waveform output provided by said detector and generating an output capnogram representation of the concentration of $CO_2$ in said breathing passage, said processing electronics further including a first integrator for providing an integration of the detector pulsed waveform output above an adjusted baseline.

40. The capnography system of claim 39 wherein said optical access includes an insert disposed in said breathing passage having at least one window disposed adjacent said LED source and at least one opposite optical element selected from the group consisting of a window and a reflector disposed across said breathing passage from said at least one window.

41. The capnography system of claim 39 further including:
a housing for said LED source and said detector removably mounted on said optical access to place said LED source and detector in radiation transmission and receiving relationship to gases in said breathing passage when mounted to said optical access.

42. The capnography system of claim 41 further including a heat source disposed within said housing providing heat to said optical access and to at lest one of said source and detector.

43. The capnography system of claim 42 including a heater regulator connected to said heat source for maintaining a temperature of the detector within said housing within approximately 0.01° C.

44. The capnography system of claim 39 wherein said processing electronics includes:
a second integrator for integrating an output of the detector between pulses; and a difference circuit for taking a difference of the integrations of said first and second integrators.

45. The capnography system of claim 44 wherein said processing electronics includes:
a sample and hold circuit connected to said processing electronics for holding the difference of the difference circuit.

46. The capnography system of claim 45 wherein said sample and hold circuit maintains each integrated pulse output between output pulses of the detector and further including:
a low pass filter connected to said circuit having a cut-off point below a pulse repetition rate of pulsed emissions from the LED source.

47. A capnography system comprising: a breathing passage for breathing gases between a patient and a breathing gas source and an exhaust;
an LED source of pulsed radiation positioned adjacent said breathing passage, the radiation having a wavelength within the absorption band of $CO_2$ gas within said breathing passage;
a detector positioned adjacent said breathing passage for detecting pulsed radiation from said LED source and providing a pulsed waveform output in response to the detected pulsed radiation from said LED source;
an optical access disposed transversely through said breathing passage providing the transmission of radiation across said breathing passage between said LED source and said detector;
processing electronics electrically connected to said detector, said processing electronics responsive to the pulsed waveform output provided by said detector and generating an output capnogram representation of the concentration of $CO_2$ in said breathing passage, said processing electronics further including a first integrator for providing an integration of the detector pulsed waveform output above an adjusted baseline;
a heater for at least one of said detector and source to limit an error in the representation of $CO_2$; and
a housing cooperative with said breathing passage for said heater, said source, and said detector for maintaining the temperature thereof.

48. The capnography system of claim 47 wherein said heater further includes control means for maintaining said temperature within a range to provide a maximum error of approximately 3 mmHg of $CO_2$ over eight hours in said capnogram representation.

49. The capnography system of claim 48 wherein said heater is in direct thermal contact with said optical access to prevent condensation on said optical access from vapor in said breathing passage.

50. The capnography system of claim 47 further including:
a housing cooperative with said breathing passage for said heater, said LED source, and said detector selectively mountable with said optical access to place said source and detector in radiation transmission and receiving relationship to gases in said breathing passage when mounted to said optical access.

51. The capnography system of claim 50 further including a conduit cooperative with said heater for directing heat from said heater within said housing to said optical access and to at least one of said source and detector.

52. The capnography system of claim 51 including a heater regulator connected to said heater for maintaining a temperature of the detector in said housing within approximately 0.01° C.

* * * * *